US00RE38155E

(19) United States
(12) Reissued Patent
Brown et al.

(10) Patent Number: US RE38,155 E
(45) Date of Reissued Patent: Jun. 24, 2003

(54) WEIGHT REDUCTION METHOD FOR DOGS AND OTHER PETS

(75) Inventors: James H. Brown, Gilbert, AZ (US); David R. Jones, Palm Beach, FL (US); Lon D. Lewis, Topeka, KS (US)

(73) Assignee: International Flora Technologies Ltd

(21) Appl. No.: 09/975,334

(22) Filed: Oct. 12, 2001

Related U.S. Patent Documents

Reissue of:
(64) Patent No.: 5,962,043
Issued: Oct. 5, 1999
Appl. No.: 08/608,766
Filed: Feb. 29, 1996

(51) Int. Cl.[7] ..... A23K 1/14; A23K 1/16; A23K 1/18

(52) U.S. Cl. ..... 426/2; 426/635; 426/648; 426/805

(58) Field of Search ..... 426/2, 630, 635, 426/648, 805

(56) References Cited

U.S. PATENT DOCUMENTS 4,310,558 A * 1/1982 Nahms ..... 426/805
5,141,755 A * 8/1992 Weisman ..... 426/805

FOREIGN PATENT DOCUMENTS

WO 94/25035 * 11/1994

OTHER PUBLICATIONS

Manos CG, et al, J. Agric. Food Chem. 34:801–804, 1986.*
Arnouts S, et al, Poultry Sci 72: 1714–21, 1993.*
Cokelaere et al, "Influence of Jojoba Meal Supplementation on Growth and Organ Function in Rats", J. Agric. Food Chem., vol. 42, pp. 1444–1448, 1993.*
Cokelaere et al, "Influence of Pure Simmondsin on the Food Intake in Rats", J. Agric. Food Chem., vol. 40, pp. 1839–1842, 1992.*
Cokelaere et al, "Fertility in Rats After Long–Term Jojoba Meal Supplementation", J. Agric. Food Chem., pp. 1449–1451, 1993.*
Cokelaere et al., "Evidences for a Satiating Effect of Defatted Jojoba Meal", Industrial Crops and Products 4, pp. 91–96, 1995.*

* cited by examiner

*Primary Examiner*—Arthur L. Corbin
(74) *Attorney, Agent, or Firm*—The Halvorson Law Firm

(57) ABSTRACT

A dog food composition containing a small but sufficient amount of simmondsin component to provide simmondsin within the range of 0.1% by weight of said dog food dry matter mix to about 1.5% by weight of said dog food dry matter mix. Also disclosed as part of the invention is a method of weight reduction of companion pets by adding to pet food the above-defined range of simmondsin, contributed by simmondsin, simmondsin analogues or mixtures thereof, such as derived from defatted jojoba seed meal, and thereafter feeding the pet food to a companion pet on a regular and sustained basis to achieve weight reduction then weight maintenance.

2 Claims, No Drawings

WEIGHT REDUCTION METHOD FOR DOGS AND OTHER PETS

Matter enclosed in heavy brackets [ ] appears in the original patent but forms no part of this reissue specification; matter printed in italics indicates the additions made by reissue.

BACKGROUND OF THE INVENTION

Obesity is the most common nutritional disease of companion pets such as dogs and cats in an affluent society. It in fact exceeds by far all deficiency diseases combined. Obesity generally is considered present when body weight of the companion pet is 15% or more greater than optimum, which is the point at which health problems begin increasing with increasing weight. It has, for example, been reported that in affluent societies from 24% to 44% of the dogs are obese. Generally speaking, the incidence of obesity in companion pets increases with the age of the pet. Similar to humans, as the animals age body fat increases, and the amount of lean body mass decreases. For dogs particularly, obesity is more common in females than males up to age 12 years.

Because obesity develops gradually, the companion pet owner is often unaware of the overweight condition until it is called to his or her attention. Rarely is an animal presented to a veterinarian solely for the problem of obesity, but instead because of dermatitis, shortness of breath, routine immunizations, or arthritic or rheumatic symptoms. It is not uncommon that obesity is the predisposing cause of the condition noticed by the owner, although the obesity itself may not be noticed. For example, in one study it was observed that nearly one-third of the owners of obese dogs did not realize that their dogs were overweight.

The cause of obesity in companion pets is quite simple—energy intake in excess of that utilized. However, the factors causing this are not quite so simple. Some dogs are known to be "easy keepers". That is, they become overweight while being fed commercial dog foods in amounts adequate for normal adult maintenance, and in the same amount and manner as their kennel mates who may maintain optimum weight.

In most instances, in companion pet obesity them an two stages—an initial phase and a static phase. The basic cause of the initial phase is a dietary energy intake in excess of that utilized, resulting in a positive energy balance which is deposited as fat. In the static phase, dietary intake is reduced in accordance with energy needs so that body weight remains constant in the obese state. Thus, the amount of food required to maintain the animal in obese state is no greater, and in fact is often less, than that required to maintain the normal, non-obese state.

Thus, the only successful way for reducing companion animals is a drastic food intake reduction. When this occurs, the companion pets often scavenge and/or beg for food because of the sensation of constant hunger. As a result, the animal finds additional food, or pet owners feed the animal to stop the begging with the result being that no weight reduction occurs.

In short, it can be seen that for companion pets successful weight reduction involves not only decreased food intake, but as well an interdisciplinary, psychological treatment that involves the interrelationship between the companion animal and its human owner. This complex psychological interdependency makes weight reduction in companion pets even more difficult than it otherwise might be. In short, success at pet weight reduction involves initially convincing the owner that weight reduction is needed; secondly, the animal's food intake must be decreased for a sustained and regular period of time sufficient for weight reduction to occur; and third, the animal must be inhibited from constant scavenging and/or begging which tempts the owner to give in and increase the food intake to stop the begging.

In the past, certain drugs have been used in the treatment of obesity in mammals, including companion pets. These include drugs which decrease appetite such as amphetamines, drugs which cause nausea, decrease intestinal absorption, or increase metabolic rate such as thyroid hormones and finally, drugs which either tranquilize or act as diuretics. None of the above have been generally effective. They often cause side effects, and tests of most have shown that such drugs are not only expensive, but ineffective in that when free choice fed with food, the animals often tend to avoid the food that contains the drug.

It therefore can be seen that there is a real and continuing need for a treatment for mammals, and especially companion pets, which is safe, efficacious, and which can successfully result in obesity reduction without changing the animal's behavioral patterns to such an extent that its relationship with its owner is changed. This invention has, as its primary objective, the fulfillment of this need.

SUMMARY OF THE INVENTION

A dog food composition containing a small but effective amount of simmondsin component to provide a simmondsin activity within the range of 0.1% by weight of said dog food mix dry matter to about 1.5% by weight of said dog food mix dry matter. Also, part of the invention is a method of weight reduction and obesity prevention of companion pets by adding pet food that contains the above-defined range of simmondsin activity, contributed by simmondsin analogues or mixtures thereof such as that synthesized or derived from jojoba seeds or defatted jojoba seed meal, and thereafter feeding the pet food to a companion pet on a regular and sustained basis until sufficient weight reduction occurs, and obesity occurrence or recurrence is prevented.

DETAILED DESCRIPTION OF THE INVENTION

Jojoba seed meal is a by-product of the oil extraction of the seeds of the jojoba plant (Simmondsia chinensis or Californica), a native oilseed shrub of the Sonoran desert, including parts of Arizona, California and Mexico. The principal product extracted from the seeds is a liquid wax with characteristics similar to sperm whale oil. Jojoba oil is frequently applied as an additive in mineral oils and cosmetics.

Defatted jojoba seed meal contains approximately 30% proteins, and its supplementation in animal feed has been reported as associated with food intake reduction and growth retardation (Booth, A. N., Elliger, C. A. and Wain, A. C., Jr., 1974. Isolation of a toxic factor from jojoba meal. Life Sci., 15: 1115–1120; Cokelaere, M. M., Buyse, J., Daenens, P., Decuypere, E., Kuhn, E. R. and Van Boven, M., 1993. Influence of jojoba seed meal supplementation on growth and organ function in rats. J. Agric. Food Chem., 41: 1444–1448). These articles indicate that jojoba seed meal contains simmondsins and suggest that it may work to induce food intake reduction by a toxic mechanism, see particularly Booth et al., 1974. Cokelaere, et al., 1993 Journal of Agricultural Food Chemistry article, reports on the influence of jojoba seed meal supplementation on growth and organ function in rats. Other articles by Cokelaere, et al.

report on the influence of pure simmondsin on food intake of rats and the effect on the fertility in rats after long-term jojoba seed meal supplementation, see Cokelaere, Influence of Pure Simmondsin on Food Intake in Rats, Journal of Agricultural Food Chemistry, 1992, 40; and Journal of Agricultural Food Chemistry, 1993, 41,1449–1451, Fertility in Rats After Long-Term Jojoba Meal Supplementation.

None of these articles suggest the use of jojoba seed meal or its simmondsin analogues in a sustained and regular weight reduction program for companion pets. It is understandable that the Cokelaere articles did not make such a suggestion since transfer of data from rat experiments to higher animals is not at all a certainty and, as well, there is a fundamental difference between successful weight reduction for companion pets and the mere observation that an active or potential active may cause food consumption reduction in some manner. For example, as illustrated in the tests hereinafter disclosed, food consumption reduction at levels within the range of 20% to 27% allows no weight reduction. Thus, for companion pets, and especially dogs, who are known to like a high calorie diet, a successful weight reduction program must involve food reduction at levels equal to or greater than 27%.

It has now surprisingly been discovered that, for reasons not yet completely understood, compounds that have simmondsin activity, and in particular defatted jojoba seed meal, when added to companion pet foods to achieve later defined levels of simmondsin activity, will successfully result in companion pet, and particularly dog, weight reduction. This is done without significantly changing the animal's behavior patterns, and importantly without changing the anima's psychological interrelationship with the pet owner. As a result, the companion pet avoids the frequent begging and/or food scavenging that destroys diet efforts and the animal will, without any significant side effects or behavior pattern changes, voluntarily practice eating habits that result in weight reduction.

In accordance with this invention, a companion pet is treated with a sufficient amount of a simmondsin component to provide from about 0.1% by weight of its daily dietary food dry matter mix to about 1.5% by weight of its daily dietary food dry matter mix of simmondsin activity. As used herein, simmondsin activity refers to a simmondsin-containing component that is present at a sufficient level to provide from about 0.1% by weight of the total dietary daily dog food mix dry matter to about 1.5% by weight of the daily dietary dog food mix dry matter of pure simmondsin. The preferred range of simmondsin activity is within the range of 0.4% by weight of said daily dietary dog food mix dry matter to about 1.0% by weight of said daily dietary dog food mix dry matter.

The simmondsin activity can be derived from jojoba seeds, defatted jojoba seed meal, from the pure compound simmondsin, from simmondsin-2'-ferulate, or from related cyanomethylene glycosides. Preferably, the simmondsin component is from defatted jojoba seed meal.

Presently, defatted jojoba seed meal is readily available, with it being a by-product of oil extraction process of the seeds of the jojoba plant. It is now normally discarded.

The method of administration or treatment with the simmondsin component can be by simply admixture (on a weight basis sufficient to provide the desired simmondsin activity) with conventional pet foods.

As those skilled in the art know, dry pet foods, typically dry dog foods, normally contain protein, fat, fiber, non-fiber carbohydrates, minerals, vitamins and moisture components. For example, as major ingredients there are typically one or two cereal grains, generally corn, wheat and/or rice. In addition, for a protein source they may contain poultry meal, by-product meat, meat and bone meal, or other animal or fish meal by-products. At times as well, grain protein supplements such as corn gluten, soybean meal or other oil seed meals may be added. Typical nutrient content in the food dry matter will be as follows. Crude protein from 14% to 50%, usually 20% to 25%. Crude fat from 5% to 25%, with current obesity management (usually containing lower fat levels such as at 5% to 8% and with super premium brands usually containing from 14% to 20% fat). Crude fiber usually is present in the range of from about 3% to 14%, usually about 5% to 7%, with the total mineral or ash content being within the range of 3% to 10%, usually 4% to 7%. The important point is not the precise formulation of the pet food, since many conventional and satisfactory ones for use in conjunction with the present invention are available on the market. Rather, the key to success is that a sufficient amount of simmondsin component be added to pet food rations, whichever formulation is used, to provide the simmondsin activity level at the ranges previously expressed.

The method of treating or administration is usually simple addition to the food prior to its extrusion or taming sufficient to provide the earlier-expressed simmondsin activity range, followed by free choice feeding of that food to the animal. However, it is conceivable that pure simmondsin, simmondsin-2'-ferulate or other cyanomethylene glycosides could be administered by injection or in tablet or powder form. However, it is currently believed that the most effective method is simple addition to normal food ration, since the result is to achieve a sufficient reduction in food intake to result in weight reduction and the prevention of obesity.

While tests have not yet been conducted on other companion pets or on other domestic livestock animals, it is conceivable and within the scope of the expected uses of the present invention that simmondsin components herein mentioned could be used successfully with other species. In fact, it is likely, although tests have not been conducted yet, that simmondsin and/or its analogues and/or its derivatives can be used as a means for successful weight reduction and obesity prevention for humans.

The following examples are offered to further illustrate, but not limit the invention.

EXAMPLES

The examples set forth below show the effects of defatted jojoba seed meal in dog food for use in weight reduction to achieve obesity correction and prevention. In these tests a high-calorie, highly-palatable, low-fiber dry dog food as currently available on the market was used. The diet was typical of a super premium dry dog food and had the following guaranteed analysis: crude protein 24–26%; crude fat 16–18%; crude fiber 3–4.5%; ash 5–6.5%; and moisture 7–9%. Defatted jojoba seed meal at a 4.5% weight level (0.37% simmondsin activity) and at an 8% weight level (0.67% simmondsin activity) was added to the diets. Simmondsin activity in the jojoba seed meal used was calculated as its percent simmondsin plus its percent simmondsin-2'-female (S2F) times S2F's simmondsin content of 68%. The jojoba seed meal also contained 4.6% didemethyl simmondsin and 1.87% dimethyl simmondsin. When 10 dogs were allowed to choose either the leading selling dry dog food or one of the diets containing defatted jojoba seed meal, all 10 dogs preferred the jojoba-containing diet (over 85% of the total amount eaten by each dog was one of the jojoba-containing diets). They consumed 31.1 times more of the 4.5% jojoba diet than they did of the leading selling dry dog food, 74.6 times more of the 8% jojoba diet than they did of the leading selling dry dog food, and 70.1 times more of the 8% jojoba diet than they did of the leading selling dry canine weight reduction diet (over 88% of the total amount eaten by each dog was the 8% jojoba diet). As evidenced from the testing shown below, simmondsin activity level of 0.37% provided by defatted jojoba seed meal added at a weight level of 4.5% of the dry dog food results in a sufficient voluntary reduction in food intake to result in maintenance of body weight by dogs that were previously known to be obese dogs and natural overeaters. The addition of defatted jojoba seed meal al the 9% by weight level which provides a simmondsin activity of 0.67% resulted in a sufficient voluntary reduction in food intake by most obese dogs to result in a 2% to 3% per week decrease in body weight. This is the rate of weight reduction most commonly recommended for obese dogs so that the pet owner notices the weight decrease, but it occurs without risk of causing any health problems in the animal. In addition, the data show that the animals do not reject the diet, but eat it regularly, seem to like it, and will continue eating it on a regular and sustained basis such as required for the desired weight reduction. Finally, no adverse effects to date in the tests have been noticed.

The dogs selected for use in this study were known to be overeaters if a palatable diet was available. They were selected for use in this study because they were specifically the type in which sobesity is a problem. The dogs are identified in following table:

TABLE I

DOGS, DIET AND METHOD USED

| Dog # | Breed Type | Initial Body Weight Lbs. | Initial Body Weight % > Opt | Optimum Wt— Lbs | Sex | Age |
|---|---|---|---|---|---|---|
| 11 | Beagle | 25.2 | 19.9 | 21.0 | F | 8 |
| 19 | Fox Terrier | 25.1 | 0 | 25.1 | F | 9 |
| 30 | Pug | 21.6 | 19.8 | 18.0 | M | 5 |
| 31 | Pug | 17.6 | 17.4 | 15.0 | M | 4 |
| 40 | English Springer Spaniel | 50.3 | 35.8 | 37.0 | F-S | 10 |
| 43 | Labrador Retriever | 80.5 | 23.8 | 65.0 | M | 8 |
| 45 | Labrador Retriever | 79.5 | 20.5 | 66.0 | F | 8 |
| 53 | Boxer | 58.7 | 2.7 | 55.0 | F | 7 |
| 54 | Labrador Retriever | 68.2 | 24.1 | 55.0 | F | 8 |
| 55 | Labrador Retriever | 76.3 | 33.8 | 57.0 | M | 8 |
| W5 | Vizsla Cross | 115.5 | 28.4 | 90.0 | M-N | 6 |
| W6 | Labrador Retriever | 62.7 | (−10.3) | 70.0 | M | 5 |
| Avg: | | 55.5 | 16.4 | 47.8 | | 7.2 |

Five diets of identical composition, except for varying amounts of defatted jojoba seed meal replacing wheat germ meal, were prepared at the same time, from the same batch of ingredients. All were similar in nutrient content, exceeding the dogs' requirements for all nutrients. The diets were all high in fat and caloric density, and low in fiber, which is the opposite in all aspects to currently-available obesity correction and prevention diets. These diets were used because the high fat content makes them especially palatable for the animal. All dogs always had water available, were allowed free access to their diet from 10:00 a.m. to 6:00 p.m. daily and were weighed at 9:00 a.m. once weekly. Food intake was measured daily. Each dog was given a thorough physical exam by a veterinarian before the study, after six weeks, and another at the end of the study.

Table II shows controlled dogs using Diet A, which contained no jojoba meal and simply was a diet without any added simmondsin activity.

TABLE II

DIET A = NO JOJOBA MEAL

| Dog No. | g eaten/kg B. wt/day. Wk 1 | Wk 2 | Wk 3 | Wk 4 |
|---|---|---|---|---|
| 19 | 33.2 | 30.8 | 22.8 | 23.1 |
| 53 | 46.0 | 29.1 | 26.1 | 25.5 |
| W6 | 51.4 | 32.5 | 32.2 | 29.8 |
| Avg. | 43.5 | 30.8 | 27.0 | 26.1 |
| % change | -21.3% | -6.0% | -3.9% | |

28 g/kg/day eaten (excluding first week)

| Dog No. | % Body Weight Change Wk 1 | Wk 2 | Wk 3 | Wk 4 | Total | % Above Opt Wt Initial | Final |
|---|---|---|---|---|---|---|---|
| 19 | +3.1 | +5.9 | (−1.8) | +1.6 | +8.9 | 0 | +8.9 |
| 53 | +11.5 | +2.4 | +0.4 | +0.2 | +14.9 | +2.7 | +18.0 |
| W6 | +10.8 | +5.8 | +4.4 | +5.5 | +29.1 | (−10.3) | +24.4 |
| Avg. | +8.5 | +4.7 | +1.0 | +2.4 | +17.6 | | |

average +2.7%/week excluding first week

| Dog No. | g/kg/day Wk 1 | % B. wt change Wk 1 | % Above Optimum Body weight on A Initial | Final |
|---|---|---|---|---|
| 45 | 36.6 | +6.0 | 13.6 | 20.5 |
| W5 | 28.5 | +10.5 | 16.1 | 28.3 |
| Avg. | 32.6 | +8.3 | 14.85 | 24.4 |

Table II demonstrates that the diet by itself, without any added simmondsin activity, was palatable, and that even after becoming accustomed to having it available, all the dogs on this control diet continued to consume excess amounts and became obese.

TABLE III

DIET D = 4.5% JOJOBA MEAL (0.37% SIMMONDSIN ACTIVITY)

| Dog No. | g eaten/kg B. wt/day Wk 1 | Wk 2 | Wk 3 |
|---|---|---|---|
| 11 | 20.0 | 19.9 | 18.7 |
| 30 | 20.4 | 16.4 | 19.1 |
| 31 | 34.7 | 22.2 | 18.9 |
| 40 | 23.8 | 16.5 | 17.3 |
| 43 | 23.4 | 18.8 | 22.1 |
| 54 | 25.6 | 22.9 | 24.1 |
| 55 | 24.4 | 23.4 | 24.5 |
| 45 | 19.4 | 21.2 | — |
| W5 | 16.4 | 17.4 | — |
| Avg. | 23.1 | 19.8 | 20.7 |

As shown, excluding the first week, dogs voluntarily reduced their food intake from 28 to 20.25 g/kg body weight/day, a 27.6% reduction, when 4.5% jojoba seed meal by weight to provide 0.37% simmondsin activity was added to the food.

TABLE IV

Diet D = 4.5% Jojoba Meal (0.3 to 0.4% Simmondsin Activity)

| Dog | % Body Weight Change | | | | | | % Above Opt Wt | |
|---|---|---|---|---|---|---|---|---|
| No. | Wk 1 | Wk 2 | Wk 3 | Wk 4 | Total | /wk | Initial | Final |
| 11 | −3.1 | −0.6 | +0.8 | — | −2.9 | −1.0 | 19.9 | 15.8 |
| 30 | −1.0 | −1.3 | −2.0 | +0.7 | −3.6 | −0.9 | 19.8 | 15.5 |
| 31 | +2.1 | −3.2 | −0.4 | — | −1.5 | −0.5 | 17.4 | 15.6 |
| 40 | −0.5 | +0.5 | −0.5 | — | −0.5 | −0.2 | 35.8 | 35.1 |
| 43 | +1.3 | −1.5 | +2.4 | — | +2.1 | +0.7 | 23.6 | 26.5 |
| 54 | +2.2 | +2.2 | −0.5 | — | +3.9 | +1.3 | 24.1 | 28.9 |
| 55 | +5.3 | −2.2 | +1.3 | — | +4.3 | +1.4 | 33.8 | 39.5 |
| 45 | 0.0 | −0.3 | — | — | −0.3 | −0.2 | 20.5 | 20.1 |
| W5 | −1.5 | +0.2 | — | — | −1.3 | −0.7 | 28.3 | 26.6 |
| Avg. | +0.5 | −0.7 | +0.16 | | +0.7 | +0.2 | 24.8 | 24.8 |

All the dogs using this diet, which differed from the Table II diet simply by the addition of 4.5% jojoba seed meal, maintained the dog's body weight even when they were allowed free access to this high energy, highly palatable diet containing 0.37% simmondsin activity. In contrast to dogs receiving the same diet without simmondsin activity, they did not continue to gain weight as the detailed evidence shows. It is worthy of note that these animals maintained weight even though they voluntarily decreased their food intake by an average of 27.6%.

In the study shown in Table V the same diet was used, except that the amount of simmondsin activity was increased to 0.67% by increasing the amount of the defatted jojoba seed meal to 8% of the diet by weight.

TABLE V

Diet E = 8.0% Jojoba Meal (0.67% Simmondsin Activity)

| Dog | g/kg body weight/day eaten | | | | |
|---|---|---|---|---|---|
| No. | Wk 1 | Wk 2 | Wk 3 | Wk 4 | Wk 5 |
| 11 | 15.5 | 15.2 | 15.5 | 14.5 | 15.6 |
| 30 | 14.0 | 10.1 | 15.1 | 7.4 | |
| 31 | 17.4 | 17.5 | 23.4 | 17.8 | 19.2 |
| 40 | 12.4 | 12.8 | 12.2 | 11.8 | 10.9 |
| 43 | 16.3 | 19.2 | 15.9 | 17.8 | 20.0 |
| 54 | 17.6 | 14.7 | 16.7 | 12.2 | 18.7 |
| 55 | 25.9 | 19.8 | 18.9 | 19.9 | 17.3 |
| 45 | 16.5 | 14.7 | 15.0 | 18.3 | 18.2 |
| W5 | 14.7 | 13.2 | 14.1 | 13.5 | 10.8 |
| 53 | 20.7 | 20.9 | 18.5 | 19.1 | |
| W6 | 15.2 | 16.5 | 16.9 | 15.4 | |
| Avg. | 16.9 | 15.9 | 16.6 | 16.0 | 16.3 = 16.34 g/kg |
| B. Wt./day eaten | | | | | |

As shown, dogs voluntarily reduced their food intake from 28 to 16.34 g/kg body wt./day, a 41.6% reduction, when 8% jojoba seed meal by weight providing 0.67% simmondsin activity was added to the food.

TABLE VI

Diet E = 8.0% Jojoba Meal (0.5 to 0.7% Simmondsin Activity)

| Dog | % Body Weight change | | | | | | | % Above or Below Opt. Wt. | |
|---|---|---|---|---|---|---|---|---|---|
| No. | Wk. 1 | Wk. 2 | Wk. 3 | Wk. 4 | Wk. 5 | Total | /Wk | Initial | Final |
| 11 | −5.0 | −2.7 | −0.8 | −1.0 | −3.4 | −12.2 | −2.4 | +15.8 | +2.2 |
| 30 | −2.3 | −4.4 | −0.2 | −7.2 | | −15.2 | −3.8 | +15.2 | 0.0 |
| 31 | −4.5 | −2.9 | −5.9 | −1.6 | −5.4 | −19.5 | −3.9 | +15.6 | (−6.9) |
| 40 | −4.0 | −1.9 | −1.2 | −5.4 | +0.7 | −11.4 | −2.3 | +35.2 | +19.7 |
| 43 | −1.5 | +0.5 | +1.1 | −2.1 | +1.3 | +0.6 | +0.1 | +24.4 | +25.4 |
| 54 | −0.6 | −2.8 | −1.5 | −2.4 | +1.7 | −5.5 | −1.1 | +28.9 | +21.8 |
| 55 | +3.5 | −2.0 | −0.8 | +0.9 | −2.5 | −0.9 | −0.2 | +39.5 | +38.2 |
| 45 | −0.9 | −1.2 | +0.5 | −3.8 | +1.3 | −4.1 | −0.8 | +20.1 | +15.2 |
| W5 | +0.5 | −1.7 | −1.9 | −0.5 | −1.4 | −4.8 | −1.0 | +26.7 | +20.6 |
| 53 | −5.6 | −5.8 | −3.5 | −7.6 | | −20.6 | −5.2 | +18.0 | (−6.4) |
| W6 | −6.4 | −2.7 | −1.7 | −2.1 | | −12.4 | −3.1 | +15.8 | +1.6 |
| Avg. | −2.44 | −2.51 | −1.45 | −2.98 | −0.96 | −9.7 | −2.2 | +23.2 | +11.9 |

As can be seen, most obese dogs using the 0.67% simmondsin activity food on a free choice basis voluntarily reduce their food intake an average of 41.6% when fed this diet, an amount sufficient to lose weight at the widely recommended rate of 2% to 3% per week. In addition, when dogs were allowed free access to the 0.37% simmondsin activity food, they were able to maintain a relatively steady weight while voluntarily decreasing their food intake an average of 27.6%. Moreover, the animals exhibited no changes in behavior and no adverse health effects during the tests. It therefore can be seen that the invention accomplishes all of its stated objectives.

What is claimed is:

1. A method of weight loss and weight maintenance in a dog, comprising:

feeding a dog a simmondain component, a simmondsin analogue, or a mixture thereof, sufficient to provide the dog pure simmondsin within the range of from about 0.4%–1.0% by weight of dog food dry matter mix until the dog reaches its target weight; and then feeding the dog a simmondsin component, a simmondsin analogue, or a mixture thereof, sufficient to provide the dog pure simmondbin within the range from about 0.1% by weight of dog food dry matter mix to about 0.37% by weight of dog food dry matter mix to maintain the dog's target weight.

2. The method of claim 1 wherein the simmondsin analogue is simmondsin-2'-ferulate or cyanomethylene glycosides.

* * * * *